United States Patent
Goh et al.

(10) Patent No.: US 8,753,872 B2
(45) Date of Patent: Jun. 17, 2014

(54) METHOD AND APPARATUS FOR ASSAY FOR MULTIPLE ANALYTES

(75) Inventors: M. Cynthia Goh, Toronto (CA); Jane B. Goh, Toronto (CA); Richard Mcaloney, Toronto (CA); Richard Loo, Toronto (CA)

(73) Assignee: Axela Inc., Etobicoke (CA)

( * ) Notice: Subject to any disclaimer, the term of this patent is extended or adjusted under 35 U.S.C. 154(b) by 1701 days.

(21) Appl. No.: 11/311,689

(22) Filed: Dec. 20, 2005

(65) Prior Publication Data
US 2006/0099649 A1    May 11, 2006

Related U.S. Application Data

(62) Division of application No. 09/814,161, filed on Mar. 22, 2001, now Pat. No. 7,008,794.

(60) Provisional application No. 60/191,344, filed on Mar. 22, 2000.

(51) Int. Cl.
| | |
|---|---|
| C12M 1/34 | (2006.01) |
| G01N 33/543 | (2006.01) |
| G01N 21/47 | (2006.01) |
| G01N 35/00 | (2006.01) |
| G01N 35/04 | (2006.01) |
| C12Q 1/68 | (2006.01) |

(52) U.S. Cl.
CPC ...... *G01N 33/54373* (2013.01); *G01N 21/4788* (2013.01); *G01N 2035/00158* (2013.01); *G01N 2035/0429* (2013.01); *G01N 33/543* (2013.01); *B01L 2300/0636* (2013.01); *B01L 2300/0819* (2013.01); *C12Q 1/6837* (2013.01); *C12Q 2565/513* (2013.01); *B01J 2219/00659* (2013.01); *Y10S 435/808* (2013.01); *Y10S 436/805* (2013.01)

USPC ... 435/287.1; 435/7.1; 435/287.2; 435/288.7; 435/808; 436/164; 436/165; 436/524; 436/525; 436/527; 436/531; 436/805; 422/82.05; 422/82.11; 356/305; 356/328; 356/334

(58) Field of Classification Search
CPC ............ C12Q 1/6837; C12Q 2565/513; B01J 2219/00659; G01N 33/54373; G01N 21/4788; G01N 2035/00158; G01N 2035/0429; G01N 33/543; G01N 21/47; B01L 2300/0636; B01L 2300/0819
USPC ................. 356/305, 328, 334; 422/57, 82.05, 422/82.11; 435/7.1, 287.1, 287.2, 288.7, 435/808; 436/164, 165, 324, 525, 527, 531, 436/805
See application file for complete search history.

(56) References Cited

U.S. PATENT DOCUMENTS

| | | |
|---|---|---|
| 4,537,861 A | 8/1985 | Elings et al. |
| 4,571,081 A | 2/1986 | Ford, Jr. |

(Continued)

FOREIGN PATENT DOCUMENTS

| | | | | |
|---|---|---|---|---|
| EP | 0416730 | * | 3/1991 | ........... G01N 33/547 |
| WO | 9843086 | | 10/1998 | |

*Primary Examiner* — Melanie Y Brown
*Assistant Examiner* — Erik B Crawford

(57) ABSTRACT

A method and apparatus for assay of multiple analytes. The method uses a sensing element comprising a substrate upon which is arranged a multiplicity of recognition elements, such that each element is laid out in a predetermined pattern. Each pattern is unique in that it can give rise to a characteristic diffraction pattern in the assay. The patterns may or may not be interpenetrating on the substrate surface. The method of detecting multiple analytes includes contacting the medium of analytes with the patterned substrate, illuminating the substrate by a light source, and detecting any resultant diffraction image. The pattern of diffraction and the intensity of the diffracted signal provides information about the existence of specific analytes and their quantification.

34 Claims, 10 Drawing Sheets

(56) References Cited

U.S. PATENT DOCUMENTS

| | | | |
|---|---|---|---|
| 4,608,344 A | 8/1986 | Carter et al. ............... 436/34 |
| 4,647,544 A | 3/1987 | Nicoli et al. |
| 4,815,843 A | 3/1989 | Tiefenthaler et al. |
| 4,876,208 A | 10/1989 | Gustafson et al. |
| 4,931,384 A | 6/1990 | Layton et al. |
| 4,989,972 A | 2/1991 | Braun |
| 4,992,385 A | 2/1991 | Godfrey |
| RE33,581 E | 4/1991 | Nicoli et al. |
| 5,014,709 A * | 5/1991 | Bjelkhagen et al. ......... 600/431 |
| 5,071,248 A | 12/1991 | Tiefenthaler et al. |
| 5,089,387 A | 2/1992 | Tsay et al. ..................... 435/6 |
| 5,118,608 A | 6/1992 | Layton et al. |
| 5,196,350 A | 3/1993 | Backman et al. |
| 5,468,606 A | 11/1995 | Bogart et al. |
| 5,478,527 A | 12/1995 | Gustafson et al. ......... 422/82.11 |
| 5,494,829 A | 2/1996 | Sandstrom et al. |
| 5,512,131 A * | 4/1996 | Kumar et al. ............... 438/738 |
| 5,541,057 A | 7/1996 | Bogart et al. |
| 5,550,063 A | 8/1996 | Bogart |
| 5,567,628 A | 10/1996 | Tarcha et al. |
| 5,585,242 A | 12/1996 | Bouma et al. .................. 435/6 |
| 5,599,668 A | 2/1997 | Stimpson et al. |
| 5,599,688 A | 2/1997 | Grass |
| 5,631,171 A | 5/1997 | Sandstrom et al. |
| 5,639,671 A | 6/1997 | Bogart et al. |
| 5,736,410 A | 4/1998 | Zarling et al. |
| 5,837,196 A | 11/1998 | Pinkel et al. |
| 5,843,651 A | 12/1998 | Stimpson et al. |
| 5,922,550 A | 7/1999 | Everhart et al. |
| 5,955,377 A | 9/1999 | Maul et al. |
| 5,986,762 A | 11/1999 | Challener |
| 5,989,923 A | 11/1999 | Lowe et al. |
| 6,060,256 A | 5/2000 | Everhart et al. |
| 6,204,068 B1 | 3/2001 | Soini et al. ................. 436/518 |
| 6,215,549 B1 | 4/2001 | Suzuki et al. ............... 356/338 |
| RE37,473 E | 12/2001 | Challener |
| 6,586,193 B2 | 7/2003 | Yguerabide et al. ......... 435/7.92 |
| 6,719,868 B1 * | 4/2004 | Schueller et al. ............ 156/272.6 |
| 2002/0028519 A1 * | 3/2002 | Yguerabide et al. ......... 436/518 |
| 2002/0037593 A1 | 3/2002 | Craighead et al. |
| 2002/0127565 A1 | 9/2002 | Cunningham et al. |
| 2002/0168295 A1 | 11/2002 | Cunningham et al. |
| 2003/0027327 A1 | 2/2003 | Cunningham et al. |
| 2003/0032039 A1 | 2/2003 | Cunningham et al. |

* cited by examiner

METHOD AND APPARATUS FOR ASSAY FOR MULTIPLE ANALYTES

CROSS REFERENCE TO RELATED PATENT APPLICATION

This patent application is a Divisional application of U.S. patent application Ser. No. 09/814,161 entitled "METHOD AND APPARATUS FOR ASSAY FOR MULTIPLE ANALYTES" filed on Mar. 22, 2001 in the name of the same inventors which claims the benefit of U.S. Provisional Patent Application Ser. No. 60/191,344 filed on Mar 22, 2000 entitled METHOD AND APPARATUS FOR MULTIPLE ANALYTES, which is incorporated herein by reference in its entirety.

FIELD OF THE INVENTION

The present invention relates to a method and apparatus for detecting multiple analytes in a medium, and more particularly the present invention relates to a method of assaying based on light diffraction which appears or changes upon the binding of analytes to their specific receptors laid out in patterns on a substrate.

BACKGROUND OF THE INVENTION

In many instances, it is desirable to determine the presence and the amount of a specific material in solution (the 'medium'). Surface-based assays rely on the interaction of the material to be assayed (the 'analyte') with a surface that results in a detectable change in any measurable property. For the purpose of this patent application, the term 'analyte' refers to the material to be assayed. Examples of analytes include: an ion; a small molecule; a large molecule or a collection of large molecules such as a protein or DNA; a cell or a collection of cells; an organism such as a bacterium or virus. 'Analyte-specific receptor, or 'recognition element' refers to that complementary element that will preferentially bind its partner analyte, This could include: a molecule or collection of molecules; a biomolecule or collection of blomolecules, such as a protein or DNA; a groove on the substrate that has the complementary geometry and/or interaction in general, in order to assay for a specific analyte, the surface is modified so as to offer the appropriate chemical interaction. In immunoassays, for example, one takes advantage of the specificity of the antibody-antigen interaction: A surface can be coated with an antigen in order to assay for the presence of its corresponding antibody in the solution. Similarly, a strand of deoxyribonucleic acid (DNA) can be attached to a substrate and used to detect the presence of its complementary strand in solution. In any of these cases, the occurrence of binding of the analyte to its recognition element on the surface, which thus identifies the presence of the specific analyte in solution, is accompanied by a detectable change. For example, the binding can produce a change in the index of refraction at the interfacial layer; this can be detected by ellipsometry or surface plasmon resonance. Alternatively, the bound analyte molecules may emit light; this emission can be collected and detected, as is the case for fluorescence-based sensors. Non-optical signals may also be used, as in the case of radio immunoassays and acoustic wave sensing devices.

Diffraction is a phenomenon that occurs due to the wave nature of light. When light hits an edge or passes through a small aperture, it is scattered in different directions. But light waves can interfere to add (constructively) and subtract (destructively) from each other, so that if light hits a non-random pattern of obstacles, the subsequent constructive and destructive interference will result in a clear and distinct diffraction pattern. A specific example is that of a diffraction grating, which is of uniformly spaced lines, typically prepared by ruling straight, parallel grooves on a surface. Light incident on such a surface produces a pattern of evenly spaced spots of high light intensity. This is called Bragg scattering, and the distance between spots (or 'Bragg scattering peaks') is a unique function of the diffraction pattern and the wavelength of the light source. There is a unique correspondence between a pattern and its diffraction image, although in practice, diffraction is best illustrated by using periodic patterns, because these yield easily recognized diffraction images of clearly defined regions of high and low light intensity.

Diffraction techniques are commonly used in studies of molecular structure; specifically, X-ray diffraction is used in the identification of chemical compounds and in the determination of protein structures. However, the principle of diffraction, especially in the optical domain, has rarely been invoked for use in assays.

U.S. Pat. No. 4,647,544 (Immunoassay using optical Interference detection) describes a light optical apparatus and method, in which a ligand, or an antibody, is arranged in a predetermined pattern, preferably stripes, on a substrate, and the binding between ligand and antiligand, or between an antibody and an antigen, is detected by an optical detector set at the Bragg scattering angle, which is expected to arise due to optical interference. The pattern of ligand or antibody is created by first laying out a uniform layer of antibody on a substrate, then deactivating sections of this coverage.

U.S. Pat. No. 4,876,208 (Diffraction immunoassay apparatus and method) describes the apparatus and reagents for an immunoassay based on a silicon or polysilicon substrate with a pattern of evenly spaced lines of a biological probe (a 'biological diffraction grating') to which binding can take place. The pattern is created by first coating the substrate with an even layer of antibodies, then deactivating regions by the use of a mask and of ultraviolet (UV) lights. This idea is extended to the assay of DNA in U.S. Pat. No. 5,089,387 (DNA probe diffraction assay and reagents), which describes a biological diffraction grating, and a process for its manufacture by first immobilizing a uniform layer of hybridizing agent on a smooth surface, and then exposing this surface to UV radiation through a mask with diffraction grating lines. The UV exposure deactivates the hybridizing agent, leaving a pattern of lines of active hybridizing agents.

The above patents on assays by diffraction are necessarily restricted to the case of a single analyte. In U.S. Pat. Nos. 4,876,208 and 5,089,387, the described techniques are extended to the case of multiple analytes by making biogratings with identical patterns of different analyte-specific receptors on different areas of a substrate and then measuring the diffraction due to each pattern measured independently of the others.

U.S. Pat. No. 5,922,550 (Biosensing devices which produce diffraction images) describes a device and method for detecting and quantifying analytes in a medium based on having a predetermined pattern of self-assembling monolayer with receptors on a polymer film coated with metal. The size of the analytes are of the same order as the wavelength of transmitted light. thereby its binding results in a diffraction pattern that is visible. This patent also describes a method of producing the patterned surface by microcontact printing of the self-assembled monolayer of receptors on a metal-coated polymer. This is extended to the case of a predetermined pattern of receptors (not necessarily self-assembling) in U.S. Pat. No. 6,060,256 (Optical Diffraction Biosensor). The technique of microcontact printing of self assembled monolayers on a metal substrate is described in U.S. Pat. No. 5,512,131 (Formation of microstamped patterns on surfaces and derivative articles).

Microcontact printing is a technique of forming patterns of micrometer dimensions on a surface using an elastomeric stamp; the material to be patterned serves as the "ink" and is transferred by contacting the stamp to the surface. Microcontact printing of proteins on silicon, silicon dioxide, polystyrene, glass and silanized glass is reported in Bernard, A; Delamarche, E.; Schmid, H.; Michel, B.; Bosshard, H. R.; Biebuyck, H.; "Printing Patterns Of Proteins" Langmuir (1998). 14, 2225-2229.

To utilize diffraction techniques in surface-based assays, it is important to be able to produce a material patterned with receptors, and the five patents discussed above have outlined their ways of doing so. In addition, other techniques that exist in the literature may be adaptable for patterning. For example, using photolithographic techniques, oligonucleotides have been immobilized on a substrate in arrays such that each array is a distinct species. U.S. Pat. Nos. 5,831,070 and 5,599,695 show how this is done through the use of deprotection agents in the gas phase. This approach has not been used in the creation of patterns for diffraction assays, but can be adapted for such with the design of an appropriate-mask.

It would be very advantageous to provide a method of simultaneously assaying for multiple analytes using diffraction of light.

SUMMARY OF THE INVENTION

An objective of the present invention is to provide a method for the simultaneous assay of multiple analytes using diffraction of light.

In accordance with this objective the present invention provides a method for detecting multiple analytes in a medium. The method involves the laying down of analyte-specific receptors on the surface of a solid substrate, such that each type of receptor defines a distinct pattern. Exposure of the substrate to a medium containing one or more analytes will result in binding events between each analyte and its analyte-specific receptor. These binding events will result in a diffraction image from which can be derived the presence of the analyte(s).

In one aspect of the invention there is provided a sensing element for use in a light diffraction assay for detecting the presence or absence of at least two analytes, comprising;

a substrate including a surface and having on said surface a first pattern comprising a first analyte-specific receptor and at least a second pattern comprising a second analyte-specific receptor, each said pattern corresponding to a diffraction pattern distinct from each other.

In another aspect of the invention there is provided a diffraction binding assay method for detecting at least two analytes, in a medium, comprising:

providing a substrate including a surface and on said surface a first pattern of a first analyte-specific receptor and at least a second pattern comprising a second analyte-specific receptor, each said pattern corresponding to a diffraction pattern distinct from each other;

contacting said surface of the substrate with the medium for a sufficient time to permit preselected analytes present in solution to bind with their analyte-specific receptors; and Illuminating said substrate and detecting light diffracted from said substrate surface and analysing said diffracted light for presence of a diffraction image representative of binding of one or more analytes with their analyte-specific receptors and identifying from said diffraction image one or more analytes present in said medium.

In this aspect of the invention illuminating the substrate may include illuminating a sufficient area of the substrate to illuminate at least a part or all of each of the at least two patterns. Alternatively, illuminating the substrate may include illuminating the patterns one a time.

In another aspect of the invention there is provided an apparatus for detection of analytes in a medium using diffraction of light, comprising:

a source of illumination;

a sensing element including a substrate having a surface and on said surface a first pattern of a first analyte-specific receptor and at least a second pattern comprising a second analyte-specific receptor, each said pattern corresponding to a diffraction pattern distinct from each other, said source of illumination being positioned so as to illuminate said substrate surface;

detection means positioned with respect to said sensing element to detect light diffracted from said illuminated surface; and processing means for analysing said diffracted light for presence of a diffraction image representative of binding of one or more analytes with their analyte-specific receptors and identifying from said diffraction image one or more analytes present in said medium.

The sensing element substrate may be transparent and have two opposed surfaces upon which analyte-specific receptors are patterned. The assay is performed by contacting both faces of the substrate with the medium, for example, by dipping.

BRIEF DESCRIPTION OF THE DRAWINGS

The invention will now be described, by way of example only, reference being had to the accompanying drawings, in which.

DETAILED DESCRIPTION OF THE INVENTION

The present invention provides a method for the assay of multiple analytes on the same general region of a substrate using light diffraction. The method takes advantage of the unique correspondence between a given pattern and its diffraction image, in order to assess the presence or absence of specific analytes. Analyte-specific receptors are laid out on the surface of a solid substrate, either directly or through an intervening layer, such that each type of receptor defines a unique pattern. For the purpose of this patent, two patterns are considered 'distinct' or 'unique' if they correspond to diffraction patterns distinguishable from each other. The solid substrate may be transparent, partially transparent, or reflecting at the wavelength of the incident illumination. In the case of a transparent substrate, analyte-specific receptors may be patterned on one or both surfaces of the substrate.

Figure 1B:
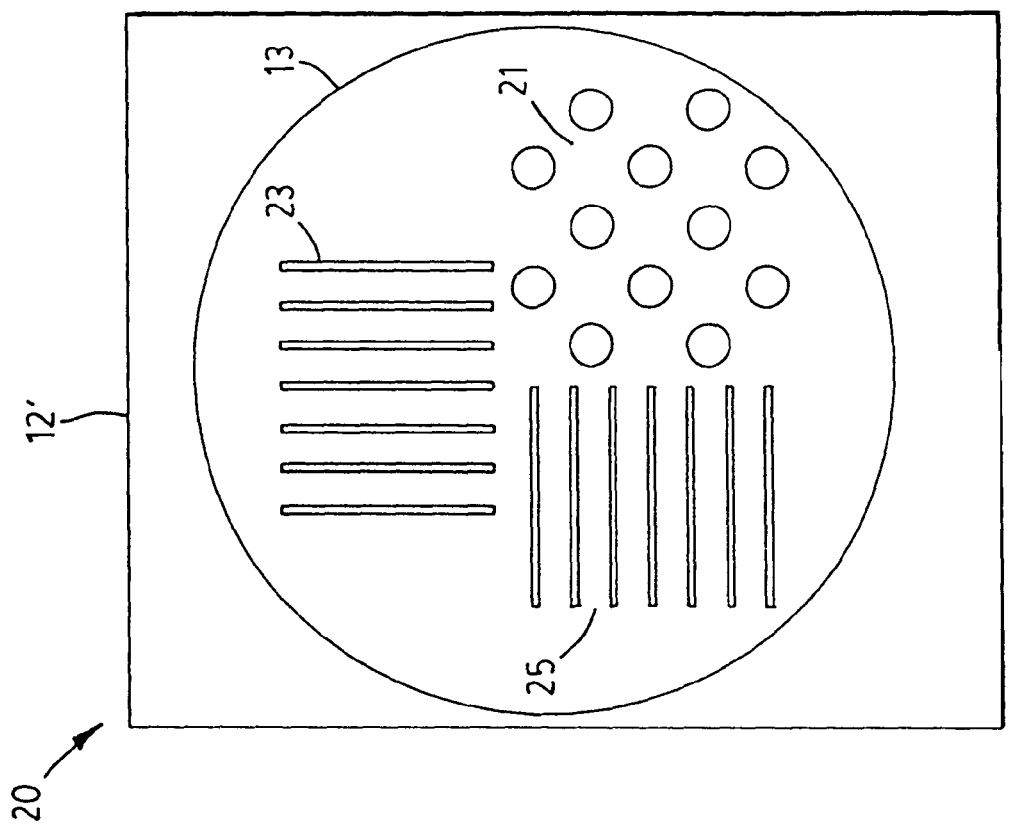
FIG. 1b is a top view of a sensing element for a diffraction assay for detecting two or more analytes having three patterns of analyte-specific receptors with the three patterns spaced from each other on the substrate surface.
Figure 1A:
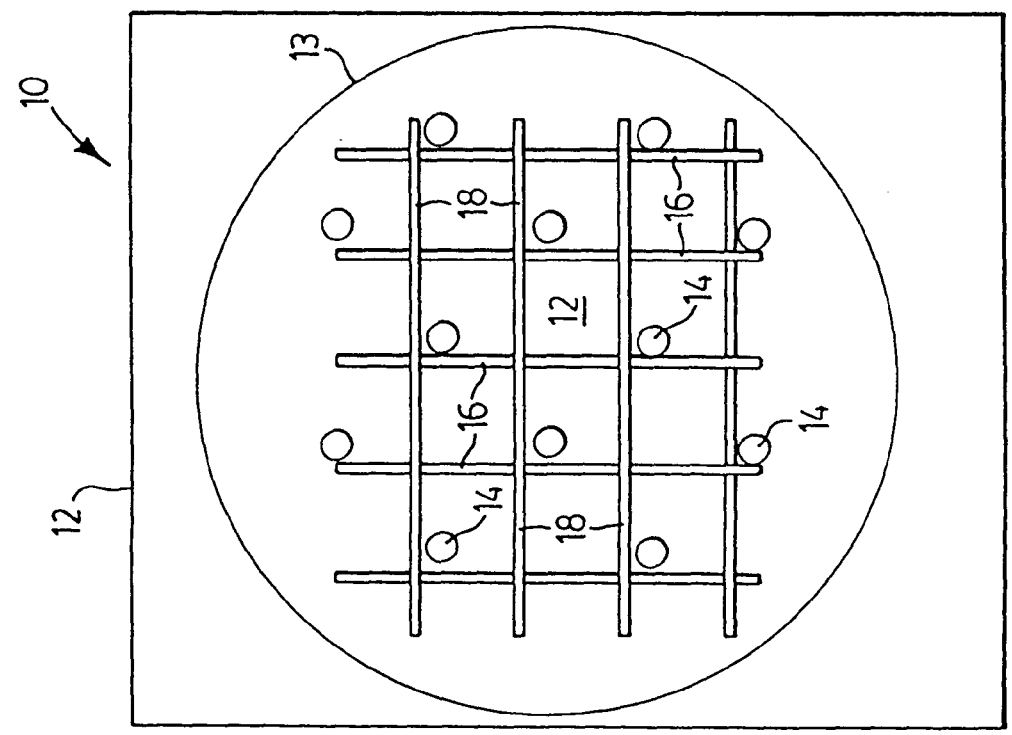
FIG. 1a is a top view of a sensing element for a diffraction assay for detecting two or more analytes having three patterns of analyte-specific receptors with the three patterns interleaved in the same area on the substrate surface.

FIGS. 1a and 1b depict general representations of two possible layouts of patterns of recognition elements on a substrate. Referring to FIG. 1a, a sensing element shown generally at 10 comprises a substrate 12 that holds multiple recognition elements, in this example there are three different recognition elements 14, 16 and 18, with each recognition element laid out in a unique pattern on the surface of the substrate. In this embodiment the patterns 14, 16 and 18 interpenetrate each other in a preselected area of the substrate 12. Under illumination, defined by the circle 13, portions of the different patterns within circle 13 are simultaneously illuminated. FIG. 1b shows another sensing element 20 having a substrate 12' having three different analyte-specific receptors laid out in three different unique patterns 21, 23 and 25 distinct from each other but in this case the patterns do not interpenetrate each other.

Once the recognition element that is capable of specific binding (e.g., protein, oligonucleotide, antibody, etc.) is laid out on the surface in a preselected patter, the medium to be assayed is contacted with the substrate, allowing analytes present in the medium to bind to their complementary recognition element. When a particular analyte is present in the medium, the subsequent binding event between analyte and its complementary recognition element is accompanied by a change in the local thickness of the layer on the substrate and/or in the local index of refraction. Both the change in thickness and the change in index of refraction will alter the optical properties at the interface between the substrate and medium in regions where the binding has taken place. Since the recognition elements are present on the substrate in a predetermined pattern, light incident on the substrate will not be scattered uniformly, but rather will be diffracted. In one embodiment of this invention, the patterned substrate is non-diffracting, and the binding events result in an observable diffraction image. In another embodiment, the patterned substrate itself produces an observable diffraction image, but the binding events alter the intensities of the diffracted signal.

The pattern of the diffracted light (the 'diffraction image') corresponds to a unique pattern on the substrate. The assay works in the following manner: The substrate is patterned with a multipilicity of analyte-specific receptors, say RA, RB, RC, such that each type of receptor defines a distinct pattern, PA, PB, PC, respectively. (Patterns are considered distinct if they individually correspond to distinguishable diffraction images, say DA, DB, DC respectively). In the case of only one type of analyte present, say AA which is complementary to receptor RA, said analyte will bind to its partner and the pattern corresponding to that of receptor RA will thus be highlighted by a change in refractive index and/or height above the substrate due to this binding event. If the patterned substrate is initially non-diffracting, the binding event will cause the appearance of a diffraction image that looks like DA. Thus, observing a diffraction image that looks like DA immediately identifies the presence of analyte AA bound to receptor RA, and hence the presence of AA in the original medium. The signal intensities at the bright regions (for example, the Bragg peaks if the pattern were a grating) reflect the amount of binding, and can be calibrated in order to effect quantification of bound analytes, and thus makes for a quantitative assay. If there are a multiplicity of analytes present, say AA, AB, AC, complementary partners to RA, RB, RC respectively, the binding events will produce a diffraction image that is a non-additive composite of DA, DB and DC. That is, patterns DA, DB and DC will be present in the observed diffraction image, but additional features will also be present. In this case, the assay can be effected in either of following manner. (1) The full diffraction image can be stored on a computer, and with the use of image processing and computational tools, the image is deconvoluted into the individual patterns. (2) In a preferred embodiment of this invention, the appearance or change in signal at specific regions of the diffraction image signify the presence of specific analytes. For example, the appearance of a bright region characteristic of DA but not DB or DC is a good marker for the presence of AA. Similar regions can be located for AB and AC, and when electronic detection is employed, their signal intensities can be calibrated (as in the case of only one analyte) in order to effect a quantitative assay. The more analytes and analyte-specific receptor patterns present, the more complex the observed diffraction image will be. It is thus important to choose patterns that are as distinct from each other as possible to enable ease of assay. As well, in simple cases, visual inspection may suffice to indicate distinctness of patterns; that is, one can clearly see that the diffraction image corresponds to DA and not DB. However, as complexity increases, a preferred embodiment of this invention uses an imaging device that will enable a more effective comparison. In one embodiment, the detector obtains the diffraction image as an electronic signal that is stored in a computer, and image processing is utilized, in another embodiment, information is already stored in the computer that will facilitate such interpretation. For example, changes in intensities at specific pixels of the image signify a particular binding event. In this latter case, this information may either be programmed in the computer or encoded in the substrate itself and be read by the apparatus during the assay.

Figure 2A:
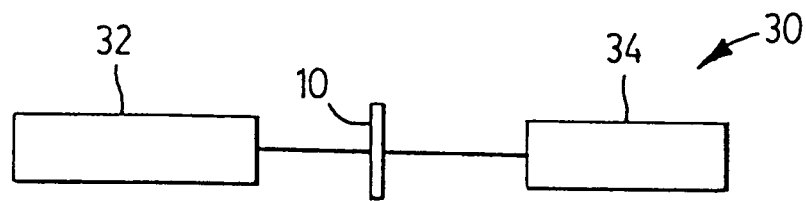
FIG. 2a shows a diagrammatic illustration of an apparatus for performing an assay in accordance with the present invention using a transmission configuration.
Figure 2B:
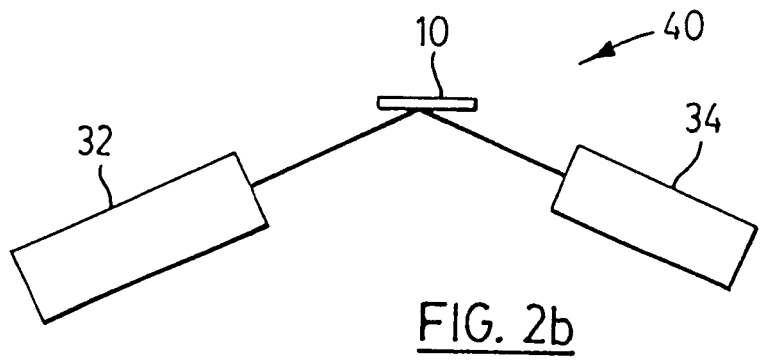
FIG. 2b shows a diagrammatic illustration of an apparatus for performing an assay using a reflection configuration.
Figure 2C:
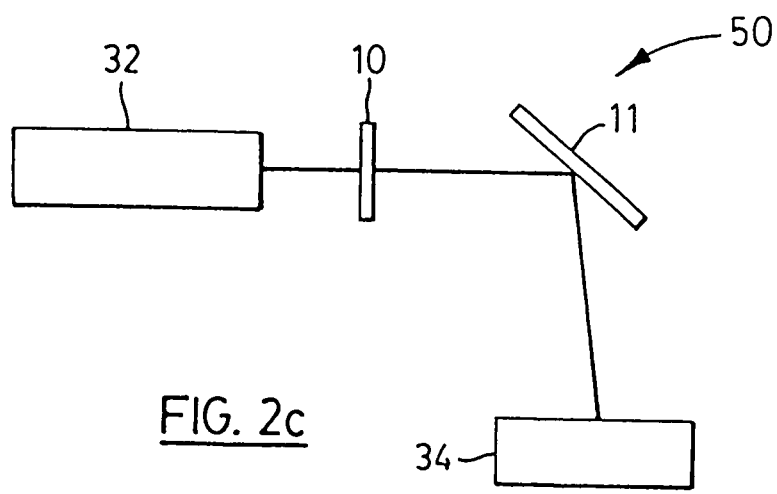
FIG. 2c shows a diagrammatic illustration of an apparatus for performing an assay using a configuration with a rotating mirror to direct the signal to a detector.

Referring to FIG. 2a, an apparatus for performing an assay in accordance with the present invention is shown generally at 30. Apparatus 30 is configured for transmission and comprises a source of illumination 32, substrate 10 with the patterned recognition elements located on a surface thereof, and a detector 34 for detecting the light after it has been transmitted through the substrate. FIG. 2b illustrates another embodiment of an apparatus at 40 constructed In accordance with the present invention that is configured for operating in reflection mode. FIG. 2c illustrates another embodiment of an apparatus 50 for use in the transmission mode including a rotating mirror 11 to direct the signal transmitted through substrate 10 to detector 34. A similar design may be used in another embodiment of a reflection configuration.

Light source 32 may produce a monochromatic beam, typically light with a wavelength in the range from the ultraviolet to the infrared, but preferably a coherent and collimated light beam, such as would come from a laser (e.g. diode, He—Ne, Nd:YVO$_4$, Argon-ion). This may be a low power, continuous wave laser. The substrate 10 may either be an optically transmitting or partially transmitting substrate with respect to the wavelength of light used in FIG. 2a or it may be reflecting or partially reflecting as shown in FIGS. 2b and 2c. In one embodiment of this invention, the incident illumination is delivered to the substrate by an optical fibre. In another embodiment of the invention, the incident illumination is scanned (rastered) over the substrate, illuminating one or more recognition elements at a time. Since each pattern is distinct and it is known a priori which analyte binds with that pattern, a detection of a change in diffraction image associated with that pattern immediately identifies the presence of that analyte.

The substrate is preferably flat or smooth enough so that impinging light will not be scattered to such an extent that it obscures or degrades the diffraction signal. Non-limiting examples of substrates that may be used are glass, mica, polished silicon, silicon dioxide, various smooth polymer materials, gold and other metals with reflecting surfaces, either as sheet or as thin films on a support. The substrate may be of any size, but the area of the active region, that which contains the patterns of analyte-specific receptors or recognition elements, should be at least the cross sectional size of the incident beam as it intercepts the surface of the substrate, and preferably of comparable size (indicated by the circles 13 in FIGS. 1a and 1b). In this way each analyte-specific receptor pattern is simultaneously illuminated so that the resulting diffraction image simultaneously gives information about the presence or absence of two or more analytes depending on the number of analyte-specific receptor patterns in the illuminated portion of the substrate.

Figure 3A:
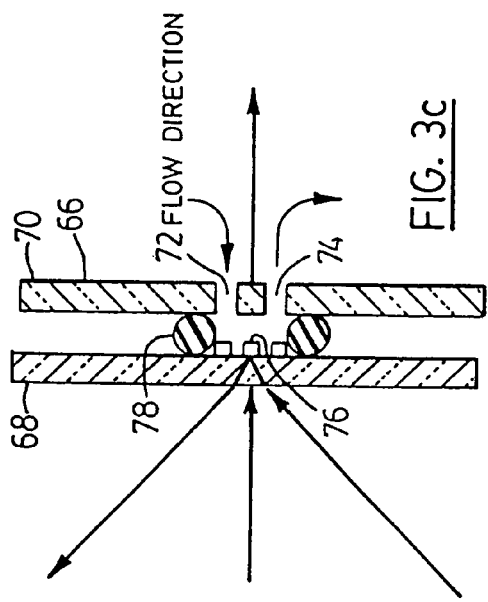
FIG. 3a is a perspective view of a cell for performing an assay in the static mode.

In applications in which moisture may be problematic, the substrate may be placed in a cell that is partially evacuated in order to reduce moisture. This is advantageous where it is desirable to reduce the signal strength that may arise due to water condensation. However, in the case where the analytes but not their partner receptors are favoured by water, the presence of water condensation (also called 'condensation figures') can be utilized to enhance the diffracted signal. In another embodiment of the invention, the assay may also be performed in situ by placing the substrate into a chamber into which the medium can be introduced. FIG. 3a shows a cell 50 with a substrate 52 immersed in a liquid being tested for the presence of one or more of the analytes in a static configuration with no flow-through. Analyte-specific receptors are patterned on one or both surfaces of substrate 52.

Figure 3B:
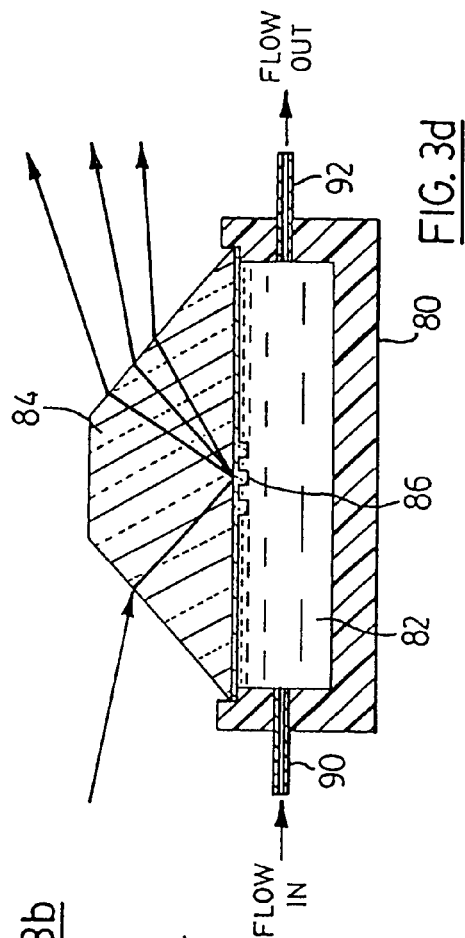
FIG. 3b is a cross-sectional view showing an embodiment of a flow cell constructed for performing the present assay.
Figure 3C:
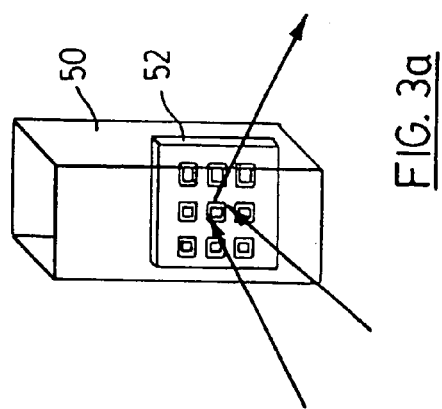
FIG. 3c is a perspective view of an alternative embodiment of a flow cell constructed in accordance with the present invention.

FIG. 3b shows a flow configuration comprising a cell 56 comprising spaced parallel walls 58 and 60 with analyte-specific receptor patterns formed on the insides of each of the walls. The liquid is continuously flowed through the cell during operation and the reflection or transmission mode may be used as indicated by the arrows. FIG. 3c shows another embodiment of a flow cell 66 comprising spaced parallel walls 68 and 70 with wall 70 having an inlet port 72 and an outlet port 74. The analyte specific receptor pattern 76 is formed on the inner surface of wall 68 and an O-ring 78 is used to seal the flow chamber. In each of these embodiments the chamber should have at least one window transparent to the incident illumination. The substrate within the chamber is located in direct line of illumination, and the assay is performed either in reflection or transmission, as described previously. In another embodiment, the fluid chamber may comprise the patterned substrate as one or more of its windows. In these embodiments, the time dependence of the binding events may be monitored simultaneously for all analytes. This may be useful for measurement of relative binding affinities.

Detector 34 must be sensitive to the illumination of choice. The detector 34 may be a position sensitive photodiode, a photomultiplier tube (PMT), a photodiode (PD), an avalanche photodiode (APD), a charged-coupled device (CCD) array, the unaided eye, a camera, a photographic plate, or any other imaging device. In one embodiment of this invention, the transmitted or reflected signal is collected by an imaging optical fibre and directed to an imaging detector. Detector 34 is attached to the appropriate accessories to provide power and enable signal collection and data processing. If a position sensitive photodiode is used it is first calibrated; the intensity of the signal reflects the position of the pattern impinging on the detector.

The photodiode, photomultiplier tube or avalanche photodiode is mounted on a translation stage. By moving the detector on the stage, the pattern of high and low light levels are mapped out. Alternatively, the PMT or (APD) may be held in a stationary position. A mirror is positioned to direct the light from the substrate to the PMT, PD or APD. This mirror is mounted on a rotation stage, and by rotating the stage, the pattern of low and high light levels can be mapped out on the PMT, PD or APD as shown in FIG. 2c.

When a CCD array or other imaging device is used, it is positioned to collect either the full diffraction image, or a part thereof. In the latter case, the imaging device is mounted on a translation stage to enable inspection of selected regions of the diffraction image; changes in the intensities signify the binding event(s).

In certain cases, as will be described in the examples hereinafter, the diffracted signal will be strong enough to be visible to the unaided eye under proper lighting conditions. In this case, all that is needed is the observer's eye, or for a more permanent record, any camera, or similar imaging device. For quantification of low intensity signals, a sensitive CCD array detector or a PMT may be used. For further signal enhancement, lock-in detection as well as amplification schemes known to those skilled in the art may be employed. As discussed previously, the image, or a part thereof, obtained as an electronic signal from the detector is stored on a computer and image analysis software is then used to identify the patterns on the substrate that gave rise to the observed diffraction image thus identifying which analytes are present in the medium. A code may be written on the substrate itself that identifies which analyte-specific receptors are present. The presence of signals at specific locations relative to a standard encoded location within the diffraction image corresponds to the presence of specific analytes. Quantification of signals at defined locations enables quantification of the amount of different analytes.

In operation, the recognition elements that are capable of specific binding (e.g., protein, oligonucleotide, antibody, etc.) are laid out on a surface in preselected patterns. The medium to be assayed is contacted with the substrate, allowing analytes present in the medium to bind to their complementary recognition element. It should be noted that the recognition element could be a structural or topographical feature such as grooves formed in the top surface of the substrate having dimensions to trap the target of interest such as a bacterium. In-one embodiment of this invention, the substrate is rinsed and dried, and placed in one of the devices previously described such that the substrate with the bound analytes is placed in direct line of the light beam from the light source 32. The substrate may be a dipstick.

Figure 3D:
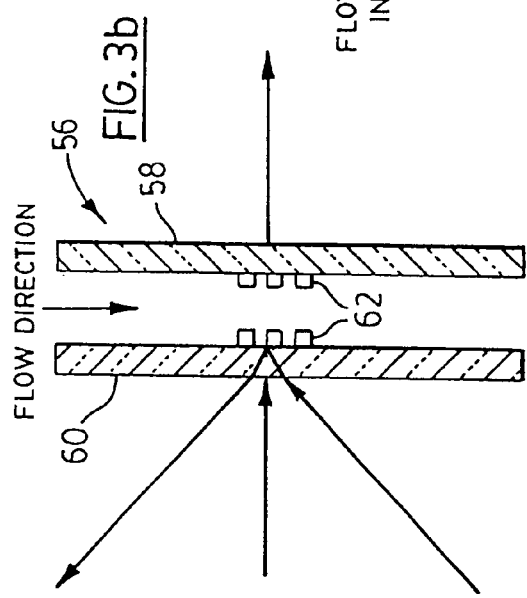
FIG. 3d is a cross-sectional view of a flow cell using total internal reflection.

While it is simplest to utilize a clear medium, such as an aqueous solution, this method can also be used for assay of analytes present in other media. The medium may generally be a fluid including gas or liquid and the analytes can include various biological pathogens, environmental toxins or chemical warfare agents dispersed in air. In one embodiment of this invention, analytes present in complex media such as urine, blood, serum, plasma or other turbid media are assayed. If the medium is not completely transparent to the incident illumination, the assay is best performed under reflection configuration. The assay of analytes in complex media may be complicated by degradation of signal-to-noise due to scattering and/or absorption of the incident illumination by the medium. Thus, in one embodiment of the invention the apparatus used to perform the assay uses total internal reflection of the incident light from the substrate-medium interface. Referring to FIG. 3d, a substrate 84 having analyte-specific receptor patterns 86 is in contact on one side thereof with the medium 82 being tested, which is contained within a chamber 80. Light is totally reflected from the interface between substrate 84 and medium 82. The cell operates as a flow cell when fluid is pumped through tube 90 into chamber 80 and out of tube 92. In another embodiment of this invention, the incident illumination is chosen so that the complex medium is transparent at the wavelength of the light, for example, the use of near-infrared laser wavelengths for the assay of fluids such as blood and the like.

The significant advantage of the present method is that by using a multiplicity of patterns, such that each type of recognition element defines a unique pattern, multiple analytes may be assayed for simultaneously using detection of light diffracted by the patterns with the preselected analytes bound thereto using light from a simple source impinging on the substrate either in reflection or transmission mode.

An exemplary, non-limiting list of analyte-specific receptors or recognition elements that may be used may be from one member of any specific binding pair, such as either member of the following pairs: antibody-antigen, enzyme-inhibitor, complementary strands of nucleic acids or oligonucleotides, receptor-hormone, receptor-effector, enzyme-substrate, enzyme-cofactor, lectin-carbohydrate, binding protein-substrate, antibody-hapten, protein-ligand, protein-nucleic acid, protein-small molecule, protein-ion, cell-antibody to cell, small molecule-antibody to small molecule, chelators to metal ions and air-born pathogens to associated air-born pathogen receptors to mention just a few. The analyte that is assayed for is thus the complementary member of the specific binding pair. Analytes may be present in a medium after processing, such as purification, isolation, amplification, for example. Alternatively, the analytes may be in fluids such as blood, serum, plasma, urine, or other body fluids.

Similarly, depending on the application and analytes that need to be identified, recognition elements may comprise small molecules that participate in non-specific but preferential binding events, as for example, a hydrogen-bonding compound, that can interact with hydrogen-bonding species over non-hydrogen bonding species, a charged species that will preferentially recognize its opposite charge. The important consideration in this case is that within a substrate with multiple recognition elements, these recognition elements can provide the desired distinction between species. For example, on the substrate there may be located one recognition element that provides a hydrogen-bonding interaction, and another that provides a hydrophobic interaction.

Each specific recognition element is arranged on the substrate to form a distinct pattern, such that the different recognition elements form different patterns on the same active region of the substrate surface that is illuminated. The presence of these patterns are preferably invisible or near-invisible to the source (that is, transmission or reflection of the source by the substrate is unaffected or minimally affected by the presence of this pattern; i.e. the pattern is non-diffracting). However, the visibility of this pattern may be adjusted by appropriate adjustment of the intensity of the source of illumination (e.g. through the use of filters), or of the detector signal (e.g. electronic filters or by software), and does not limit the scope of the invention.

In the present invention, we utilize patterns that correspond to diffraction patterns that are different from each other. This is not a fundamental issue, but simply one of ease of detection. That is, given a perfect detector, which can capture the full diffraction image to infinite resolution, this image can be deconvoluted into the set of surface patterns that gave rise to it; in practice, one should choose surface patterns that can be easily differentiated, as well as can be made with reasonable ease. The following are non-limiting examples of simple distinct patterns: (1) they may consist of different geometric elements (lines, circles, etc.); (2) they may be of the same geometric elements but arranged with different periodicities: (3) they may be of the same geometric elements with the same periodicity but rotated with respect to each other, provided the patterns do not have rotational symmetry: (4) they may be a mixture of any of the above. The size and shape of the elements in a pattern, and their periodicities determine the resulting diffraction image, as is discussed in many textbooks in optics (for example: E. Hecht, "Optics", $2^{nd}$ edition, Addison-Wesley, 1987) and known to those skilled in the art.

The patterned layer itself may be invisible to the source for several reasons, including that the layer of recognition elements is very thin and its refractive index is closely matched to that of the substrate. If the layer of recognition elements is not very thin with regards to the original substrate, an inert material can be added, such that this inert material covers the rest of the substrate, and reduces the effective thickness of the patterned layer. In this case, the refractive index of the patterned layer and of the inert material should be closely matched. Another reason the patterned layer may not be visible to the source is that the layer of recognition elements is very thin and the refractive indices of the substrate, the thin layer and medium are very similar.

If the conditions above are not met, the patterned layer may produce a weak diffraction signal prior to addition of the analyte. In this case, a binding event is accompanied by an enhancement in diffraction signal, and detection of the analyte is accomplished by observing the changes in the signal intensities of selected parts of the diffraction image. Alternatively, the light source can be reduced in intensity, either by controlling its input power, or by the use of optical filters, so as to null this background diffraction pattern that arises from the recognition elements. The enhanced signal due to binding will thus cause a positive signal on the detector.

It may be very useful to detect light diffracted from the substrate surface prior to exposure of the substrate surface to the medium being screened for the purpose of producing a baseline diffraction image due to the substrate and analyte-specific receptor patterns in the absence of analytes. This baseline baseline diffraction image is then stored and compared in the appropriate way to the diffraction image obtained after exposure of the substrate to the medium.

Alternatively, the initial patterned substrate may produce a diffracted image, and the analyte may interact with the recognition elements on the substrate that would result in the decrease of the diffracted signal. One example is the case where the recognition elements are probe molecules that are degraded by the analyte. Another example is the case where the recognition elements are grooves or other types of surface relief patterns or topographical features on the substrate, which are filled in by the binding of the analytes. Such interaction would then be detectable by the disappearance or decrease in brightness of specific regions within the diffraction image.

The device can quantitatively determine the amount of analyte in the original solution by measurement of intensities at the appropriate parts of the diffraction image. Each type of analyte, when bound to its partner receptor, defines a specific diffraction pattern, and thus gives rise to certain characteristic parts of the resulting diffraction image. Different analytes can thus be quantified by examination of the intensity of the appropriate parts of the diffraction image. The way to effect quantification is by calibration with standard analyte samples of known concentration. The utilization of calibration curves for quantification purposes is typical of immunoassay methods.

The diffracted signal strength may be enhanced by the addition of one or more secondary species selected to localize on the already immobilized analytes. The secondary species may contain a substance that will enhance the change in index of refraction (such as a chromophore, a metal colloid with a plasmon band, resonant with the source wavelength, or an enzyme that can cause a precipitate to form when appropriate reagents are added), or enhance the change in height above the substrate (such as a large particle, a metal colloid, a polymer colloid, a quantum dot, a protein), or both.

Alternatively, the analytes may be pre-treated so as to be first coupled to a material that will enhance the signal obtained upon binding, either through a change in refractive index, or in height, or both. This material may be a polymer colloid, a large molecule, a chromophore or a metal colloid. The chromophore or metal colloid should preferably absorb radiation at the wavelength of the source illumination.

The patterns of recognition elements on the surface may be created in any of several ways, depending on the specific analyte to be assayed. Example methods include microlithography and its variations, microcontact printing, ink-jet writing, robotics spotting, dip pen nanolithography, nanolithography by atomic force microscopy, near-field optical scanning lithography. These various techniques are described in more detail hereinafter.

Microlithographic techniques are well known to those skilled in the art. For example, masking strategies and reactions developed for the creation of DNA arrays, as described in U.S. Pat. Nos. 5,599,695; 5,753,788; 5,831,070; 4,867,208 and 5,089,387 may also be employed here. The main difference is that in these previous patents, different types of oligonucleotides are placed on different spatial regions on the substrate by using a mask that exposes one region of interest at a time. In the current invention, masks corresponding to various patterns are used to prepare a multiplicity of oligonucleotide patterns on the same total area.

Microlithography can also be used to create patterns on self-assembled monolayers (SAM) of thiol on gold. Using the appropriate mask, SAMs of thiol on gold can be exposed to UV light. Areas that are not covered by the mask undergo a reaction and the thiols are desorbed and can be washed off to leave a bare gold surface. A different thiol can then be adsorbed on these exposed gold regions. These thiols may already contain the receptor elements or can be derivatized subsequently by common methods. Thus, iterative processing using different masks and different thiols result in multiple patterns in the same area.

Microcontact printing is a stamping technique, in which the ink is transferred from an elastomeric stamp, such as polydimethylsiloxane (PDMS), to the desired substrate. The stamp is prepared by casting the precursor polymer on a master, and subsequent curing to harden it. The master is typically a hard material which has topographic features corresponding to the desired patter.

The use of self-assembled monolayers as the ink to form a patterned monolayer on metals such as gold by microstamping or microcontact printing is described in U.S. Pat. No. 5,512,131. Patterning of polymer substrates by self-assembled monolayers is feasible through the use of a thin metal film that is deposited on the polymer; this is described in U.S. Pat. No. 6,020,047. In particular, the stamping technique has been used to create protein patterns on silicon, polystyrene and silanized glass, as described in Bernard, A; Delamarche, E.; Schmid, H.; Michel, B.; Bosshard, H. R.; Biebuyck, H.; "Printing Patterns Of Proteins" Langmuir (1998), 14, 2225-2229.

In order to create multiple recognition elements on the same substrate, different stamps are used for each element. The stamps vary in the geometric structure they contain (lines, circles, etc,) and/or the periodicity of the patterns. Alternatively, in the case of patterns lacking in-plane rotational symmetry (such as lines), the same exact same pattern may be used, but different recognition elements are stamped at different angles with respect to each other.

Patterns may be 'written' on a substrate using current technology of inkjet printers, or by the use of computer-controlled robot arm, or by an analog plotter with fine point. In any of these cases, the substance to be patterned, either the recognition element or its precursor, is in a liquid medium and is deposited by dropping the solution at the desired locations. The solution is allowed to dry, so that the recognition elements are adsorbed onto the substrate, and excess material is rinsed off. Alternatively, a chemical or photochemical reaction is used to covalently bind the recognition elements at the appropriate location, subsequent to writing the pattern. In one embodiment of this process, the substrate surface is first activated by being coated with a reactive layer. This method is suitable for creating patterns whose elements are of the order of tens of microns in their smallest dimension.

When it is preferred to use smaller patterns, such as to increase the number of patterns in a given area, advances in scanning probe microscopy approaches are utilized. Dip pen nanolithography is based on the strong preferential adsorption of certain molecules to form self-assembled monolayers, such as thiols, bound to metals such as gold. Thus, a pen dipped in a dilute solution of thiols can pick up some molecules. By contacting such 'ink' to a gold surface, a monolayer of thiols is strongly immobilized at the point of contact. By using a small point, such as the probe tip of an atomic force microscope, structures (consisting of a monolayer of materials) that are tens of nanometer in size can be 'written' on a metal substrate. The technique of dip pen nanolithography is described in Piner, R. D.; Zhu, J.; Xu, F.; Hong, S. H.; Mirkin, C. A. Science 1999, 283, 661-663. In particular, a derivative of biotin that has a dithiol linkage can be patterned in this manner. By using the known avidin-biotin Interaction, other materials can be immobilized in a pattern dictated by the initial biotin layer.

Atomic force microscopy (AFM) can be used to pattern proteins on surfaces by the simple procedure of allowing protein adsorption, then using the AFM probe tip to scratch off regions so as to produce the desired pattern. This sample is then backfilled by contacting with a solution of another recognition element. A description of this approach in the case of thiols and carboxylic acids is given in U.S. Pat. No. 5,922,214, and extended to proteins in Wadu-Mesthrige, K.; Xu, S.; Amro, N. A.; Liu, G. Y.; Langmuir 1999, 15 8580-8583.

In one embodiment of pattern formation, the recognition elements are laid out directly on the substrate by any of the techniques described above or by other means. In another embodiment of pattern formation, an intervening layer is used that will assist in the patterning. One example is the use of the known biotin-avidin affinity as follows. A pattern of biotin is 'written' on the substrate. This is then contacted with a solution of streptavidin, which binds selectively to the biotin layer. After washing off excess protein, this sample, which now has a patterned layer of streptavidin-biotin, is then contacted with a solution of a biotinylated recognition element, which binds to the patterned streptavidin, creating a patterned recognition element. The process is then iterated to produce the second pattern of a second recognition element, and so on.

The patterning of the initial biotin layer can be produced in many of the ways describe above. A preferred embodiment is the use of either microcontact printing or dip pen nanolithography using a dithiol compound on a metal or metal film as substrate. Another relies on the use of photobiotin, which is a light-activated form, in conjunction with lithographic techniques, see Hengsakul, M.: Cass, A. E. G.; Bioconjugate Chemistry, 1996, 7, 249-254.

Another embodiment is the use of microcontact printing of an activated form of biotin on a substrate with which it can interact, and preferably react. An example of this substrate is glass coated with an aminosilane layer.

In another embodiment of the invention, the pattern of recognition elements that is overlayed on a substrate that is also topographically patterned with crevices. The substrate is preferably a polymer that has several different topographical patterns; the topographic patterns may be produced by micromachining or by microlithography and etching. On each pattern there is immobilized one recognition element. The polymer substrate is chosen such that its index of refraction matches that of the solution of analytes. Alternatively, the medium's refractive index is adjusted to match that of the patterned substrate. In either case, the assay is performed in the following manner. The patterned substrate is placed in a cell with flat windows, which is illuminated by the source. The medium containing the analytes to be assayed is then introduced. At the initial time, no diffraction image is observed because of refractive index matching between the substrate and the medium. As the binding event takes place, a diffraction pattern emerges, which is characteristic of the pattern to which the appropriate analyte binds.

The invention may be utilized as an indicator of presence or absence of a specific analyte. In one embodiment of the invention, the amount of analyte is determined by measurement of the intensities of the light in the portion of the diffraction image that corresponds to the specific analyte. This is preferably done by first producing a calibration curve. In another embodiment this signal intensity is monitored as a function of time after introduction of the analyte; from this can be obtained information about kinetics of the binding. The binding of two or more analytes to their analyte-specific receptors can be compared within the same substrate. In this embodiment of the invention, the time dependence of the intensities of portions of the diffraction pattern that can be ascribed to specific analytes are compared.

The apparatus and method described herein is applicable to assay various combinations of analytes. Substrates patterned with different sets of analyte-specific receptors can thus be prepared and used within the same apparatus. In one embodiment of this invention, the substrate is encoded with markings that identifies which type of receptors are patterned within it, and hence which analytes it can be used to assay. In another embodiment of this invention, the substrate is encoded with information regarding which specific locations within the diffraction image relative to a standard location should be used to assay for specific analytes. The diffraction image thus recorded can be analyzed with this prior information already available to the instrument.

The method of detecting multiple analytes disclosed herein is advantageous for several reasons. It is possible to perform an assay for a multitude of analytes using a very small sample depending on the resolution of the pattern printing methodology. For example, the active area of the substrate may be as small as, or smaller than, 1 mm on a side. The sample amount required will then be as small as, or smaller than, 1 mm×1 mm×thickness of the pattern. The method is advantageous because of increased reliability due to repetition of elements within a pattern and the method is quite inexpensive. The sensing elements 10 may be produced in bulk with the analyte-specific receptors being dependent on the analyte the user requires.

The method disclosed herein may be utilized for numerous applications. It may be used as an alternative or complement to a DNA array. A plurality of patterns, each one containing a specific sequence of oligonucleotide or nucleic acid, is laid out on a small region (typically a millimeter, or less.) The method may be used for rapid medical diagnostic applications, for example rapid analysis of body fluids, such that several different tests can be performed with the same (small) sample and at the same time.

This method is of great benefit when diagnosing a specific syndrome that has multiple markers. For example, red tide outbreak is marked by the presence of any of several toxins. It is very useful for differential assays, that is, in cases where a comparison between the amount of A, B, C etc. are needed in the same sample. It may be used for binding assays of multiple analytes. In one embodiment of this invention, one of the analyte-specific receptor may be a marker for an analyte that serves as a standard that identifies the material, or that serves to calibrate the instrument. The present method may also be adapted so that time dependence of the binding events can be monitored. The following non-limiting examples are intended to illustrate the present invention and in no way are to be considered limitations on the scope of the present invention.

EXAMPLE 1

Preparation of Patterned Substrate by Microcontact Printing

Figure 4:
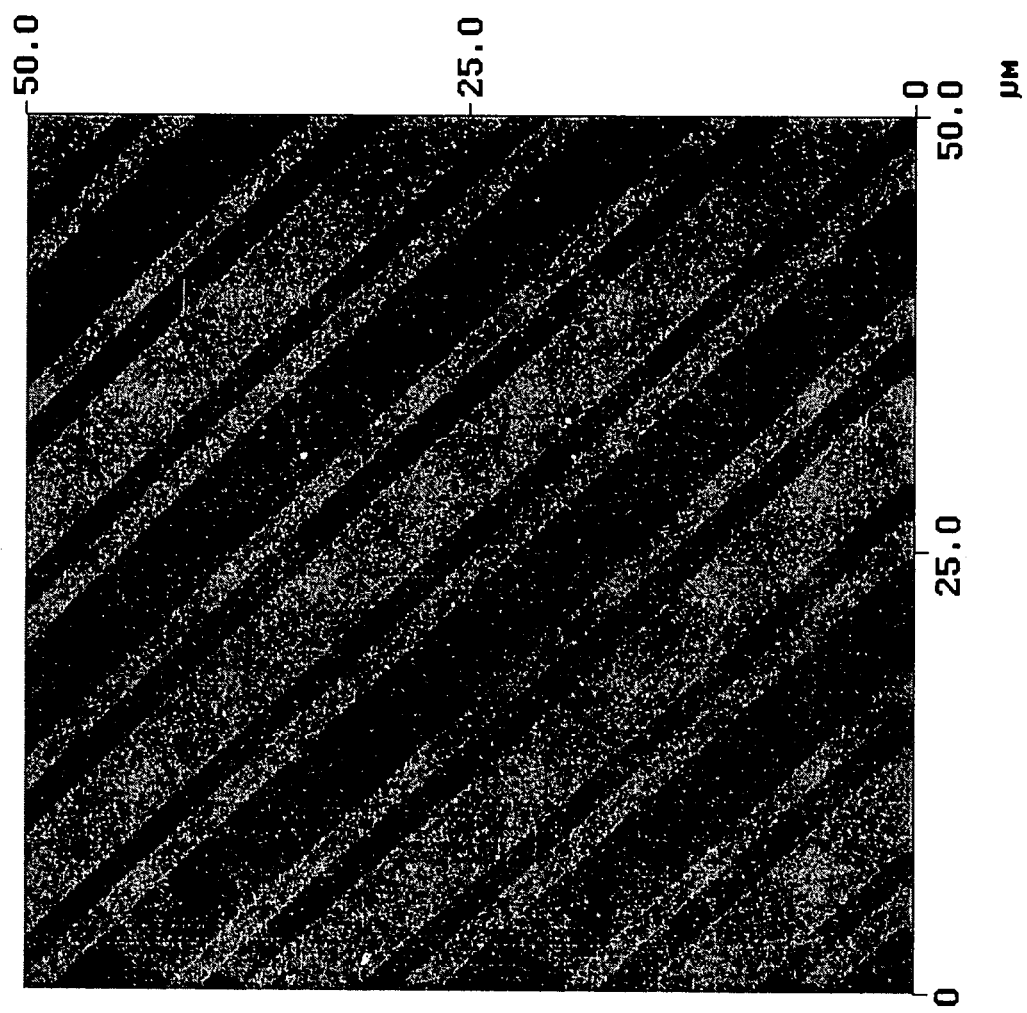
FIG. 4 shows a glass substrate patterned with goat immunoglobulin G (IgG) by microcontact printing, visualized by atomic force microscopy.

The substrates were patterned by microcontact printing following the procedure described in Bernard, A; Delamarche, E.; Schmid, H.; Michel, B.; Bosshard, H. R.; Biebuyck, H.; "Printing Patterns Of Proteins" Langmuir (1998), 14, 2225-2229. The poly(dimethylsiloxane) (PDMS) stamps were fabricated by using as molds acrylic diffractive optic masters (G1007A and G1008A, Thor Labs) using typically 10% crosslinking (Sylgard 184 Silicone elastomer kit, Dow Corning Corporation purchased from Paisley Products, Ontario Canada) and curing at 50-60° C. for 14-18 h. The PDMS stamps prepared in this manner have a diffractive surface of ~50 $mm^2$. The PDMS stamp was cleaned by sonication in a 2:1 solution of distilled and deionized water ($ddH_2O$)/ethanol for 5-10 min, followed by drying under a stream of nitrogen gas ($N_2$) and applying a fresh piece of adhesive tape to the stamp surface. The tape was removed from the stamp surface after a few minutes. 150-200 µL of protein at 50-100 µg/mL in phosphate buffered saline (PBS) was immediately applied to the stamp surface and allowed to stand at room temperature. After 30 min, the solution of protein was removed and the inked stamp surface was washed with PBS (2×2 mL). $ddH_2O$ (2×2 mL) and, finally, dried under a stream of $N_2$. The stamp was then applied under light pressure to a substrate, previously cleaned by sonication in 2:1 $ddH_2O$/EtOH and dried under a stream of $N_2$, and left in place for several seconds. The stamped substrate was then washed with PBS (2 mL), $ddH_2O$ (2 mL) and dried under a stream of $N_2$. A substrate prepared in this manner is shown in FIG. 4, where the deposited material is visualized using atomic force microscopy.

Figure 5:
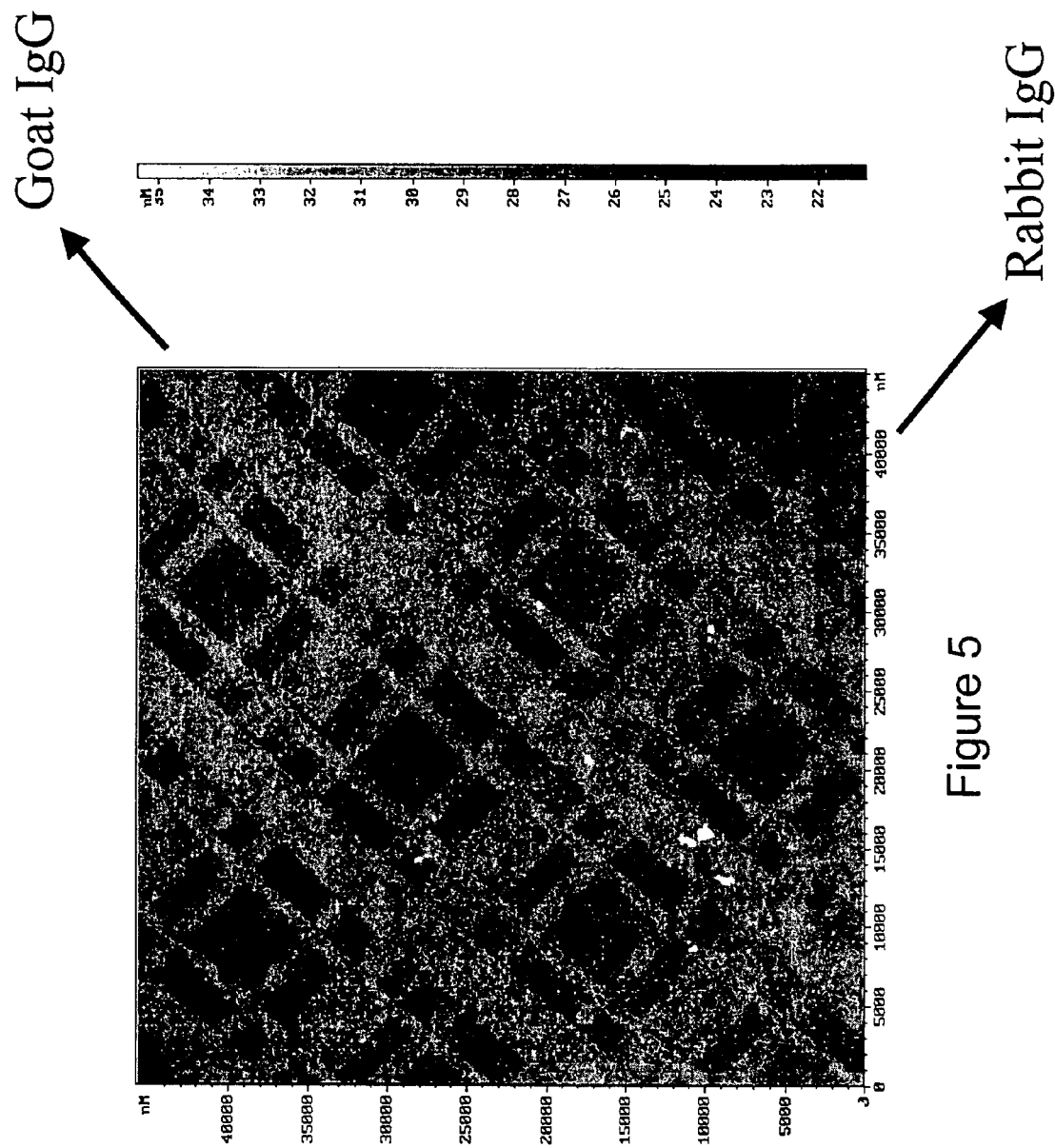
FIG. 5 shows a glass substrate patterned with goat IgG and rabbit IgG produced by microcontact printing using a stamp for both having the same pattern but rotated ~90° with respect to each other, the images being obtained by atomic force microscopy.

Subsequent patterns were produced on the same substrate by using additional PDMS stamps cleaned, inked and stamped in the same manner as above, but cross-stamped onto the substrate at angles offset from the existing patterns. FIG. 5 shows an example of a substrate prepared with two analytes stamped on the same region using the same stamp pattern but rotated with respect to each other, as visualized by atomic force microscopy.

EXAMPLE 2

Signal Measurement

The substrate was illuminated with either a Nd:$YVO_4$ laser (λ=532 nm) or a red diode laser (λ=650 nm). The diffraction image of crossed-stamped substrates resulting from illumination by either laser can be visually observed in transmission or reflection mode prior to addition of analyte. For visual and photographic signal detection, the intensity of the diffracted light was reduced to the point when the diffraction image was no longer discernible by eye using a neutral density filter before the addition of analyte. For electronic signal detection, the intensity was reduced with a neutral density filter to a small, but measurable value to maximize the signal range of the detection device before the addition of analyte.

EXAMPLE 3

"Dry" Measurement

In the "dry" measurement scheme, the substrate was immersed in a solution containing the analyte for the specified period of time. The substrate was then removed from the analyte solution, washed with PBS (2 mL) and $ddH_2O$ (2 mL), and dried under a stream of $N_2$. The substrate was illuminated with a laser and a visible diffraction image could be discerned by eye and the intensity measured using a CCD linear array or CCD area array detector hooked up to a computer. Alternatively, a photomultiplier tube mounted on an x-y translation stage was used to measure the signal intensity of a specific spot on the diffraction image by moving it across the spot while recording the intensity on an oscilloscope.

EXAMPLE 4

In Situ Measurement

In situ measurements were done in either a low volume (10-20 µL) or high volume (100-200 µL) arrangement. The low volume configuration consisted of a 10 mm×10 mm substrate held in place with two pieces of double-sided adhesive tape against a microscope slide with the stamped substrate surface facing the microscope slide. A channel of 1 mm×5 mm×10 mm was formed by the two pieces of double-sided sticky tape through which analyte solution can be wicked into contact with the stamped surface of the substrate. In the high volume configuration, the substrate was separated from a plastic backing with a rubber O-ring such as shown in FIG. 3c. Two holes were drilled into the plastic backing through which analyte solution could be added and removed. The total volume of this cell is ~100-200 µL. In both these configurations, the diffraction signal is measured after illumination of the substrate by the lasers in reflection mode.

The intensity of the diffraction image is reduced when the substrate is immersed in an aqueous solution compared to when the substrate is dry and in air. As measured by a CCD linear array coupled to an oscilloscope, a 900 mV signal in air drops to 580 mV upon addition of 1×PBS solution to the cell.

EXAMPLE 5

Goat and Rabbit IgG Stamped Substrate Tested with Anti-Goat and Anti-Rabbit Gold Conjugates Goat and rabbit IgG were cross-stamped onto a glass substrate as described above. See FIG. 5 for an AFM image of the cross-stamped substrate. The resulting cross-stamped slide was immersed in anti-goat IgG gold conjugate solution for 30-60 min and then removed from the solution of anti-goat IgG gold conjugate and washed with PBS (2×2 ml) and $ddH_2O$ (2×2 ml) and dried under a stream of $N_2$. The development of the diffraction images observed in both the transmitted and reflected modes corresponding to goat IgG on the substrate was monitored visually (data not shown). The stamp was then immersed in an anti-rabbit IgG gold conjugate solution for 30-60 min and then removed from the solution of anti-rabbit IgG gold conjugate and washed with PBS (2×2 ml) and $ddH_2O$ (2×2 ml) and dried under a stream of $N_2$. The development of the diffraction images observed in both the transmitted and reflected modes corresponding to rabbit IgG on the substrate was monitored visually (data not shown).

EXAMPLE 6

Goat and Rabbit IgG Stamped Substrate Tested with Anti-Goat and Anti-Rabbit IgG

Goat and rabbit IgG were cross-stamped onto a substrate as described above. The resulting cross-stamped slide was immersed in anti-goat IgG solution for 30-60 min and then removed from the solution of anti-goat IgG and washed with PBS (2×2 ml) and $ddH_2O$ (2×2 ml) and dried under a stream of $N_2$. The development of diffraction images from both transmission and reflection mode measurements corresponding to goat IgG on the substrate was observed visually (data not shown). The stamp was then immersed in an anti-rabbit IgG solution for 30-60 min and then removed from the solution of anti-rabbit IgG and washed with PBS (2×2 ml) and ddH$_2$O (2×2 ml) and dried under a stream of N$_2$. The development of diffraction images from both transmission and reflection mode measurements corresponding to rabbit IgG on the substrate was observed visually (data not shown).

EXAMPLE 7

Figure 6:
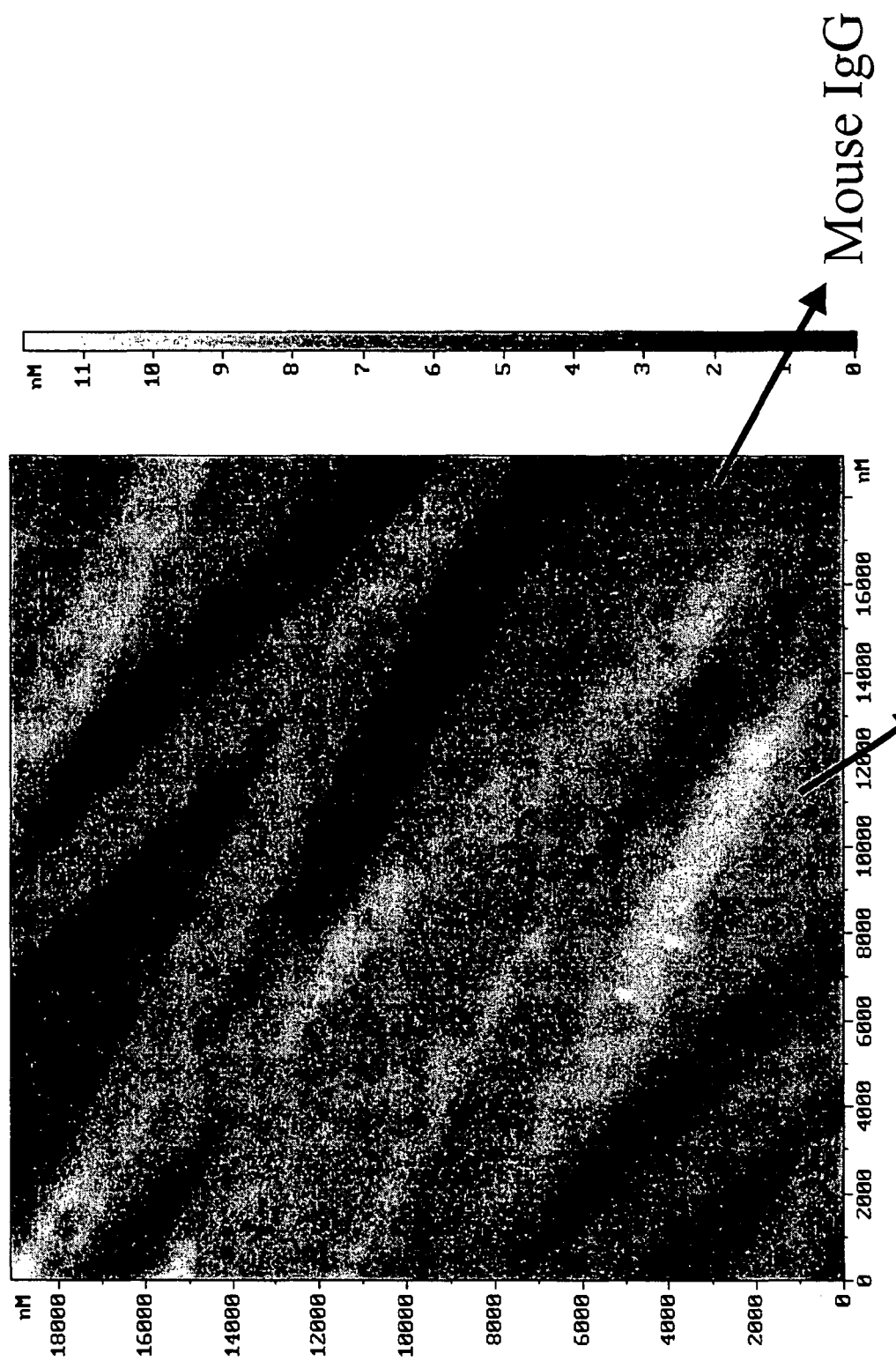
FIG. 6 shows a glass substrate patterned with mouse IgG and rabbit IgG produced by microcontact printing using a stamp for both having the same pattern but rotated ~30° with respect to each other, the images being obtained by atomic force microscopy.

Rabbit and Mouse IgG Stamped Substrate Tested with Anti-Rabbit and Anti-Mouse IgG Rabbit and mouse IgG were cross-stamped onto a substrate as described above. FIG. 6 is an AFM image of the cross-stamped substrate. The resulting cross-stamped slide was immersed in a solution of goat anti-rabbit IgG for 60 min and then washed with PBS (2×2 ml) and ddH$_2$O (2×2 ml) and dried under a stream of N$_2$. The substrate was then immersed in a solution of goat anti-mouse IgG for 60 min and then washed with PBS (2×2 ml) and ddH$_2$O (2×2 ml) and dried under a stream of N$_2$. Finally, the substrate was immersed in a solution of rabbit anti-goat IgG for 60 min and then washed with PBS (2×2 ml) and ddH$_2$O (2×2 ml) and dried under a stream of N$_2$. The anti-goat IgG treatment was used to enhance the existing signals through a "sandwich" assay. The intensity of a characteristic spot in the diffraction image was measured after each incubation/wash cycle.

Figure 7:
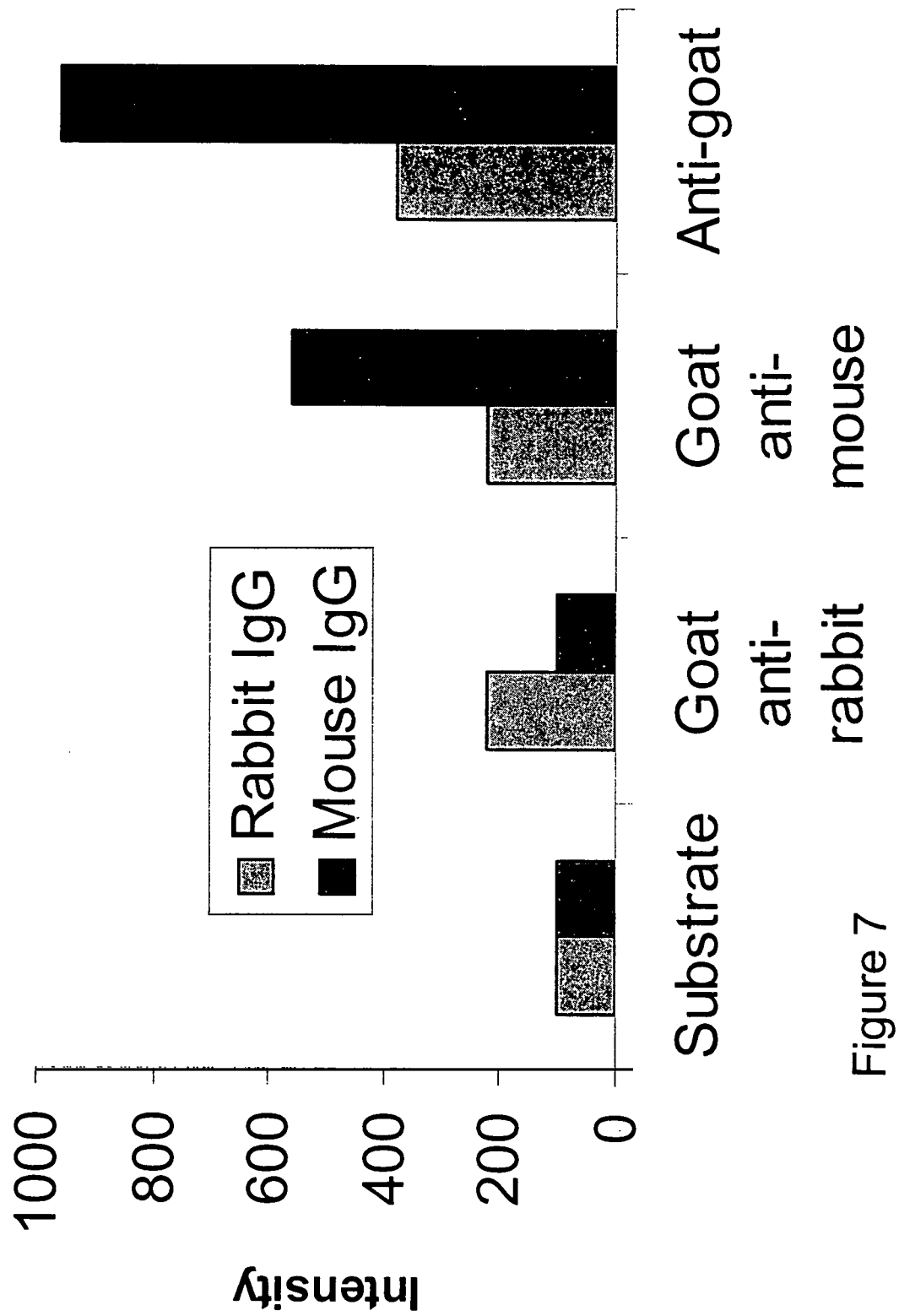
FIG. 7 shows effect of treating a rabbit and mouse IgG cross-stamped substrate sequentially with the indicated solutions.

FIG. 7 shows effect of treating a rabbit and mouse IgG cross-stamped substrate sequentially with the indicated solutions. The diffraction image consists of two bright rows of dots perpendicular to each other (other periodic patterns of dots can be seen, but they are much weaker in intensity). One row of dots is characteristic of the rabbit IgG pattern, while the other is due to the mouse IgG. The intensities at two locations in this diffraction image, one of the bright dots corresponding to rabbit and one corresponding to mouse IgG, were measured with a linear CCD array detector attached to an oscilloscope. Prior to introduction of the analytes, the substrate gives a low intensity reading for both spots. Addition of goat anti-rabbit IgG results in an increase in the signal arising from the stamped rabbit IgG, while little change is observed in the signal that derives from mouse IgG. Treatment of the substrate with goat anti-mouse IgG then results in the increase in signal that arises from stamped mouse IgG, while the signal for rabbit IgG remains constant from the previous treatment. Finally, the addition of anti-goat IgG to the previously treated substrate results in the further increase of both signals, confirming that the goat-raised antibodies used in the first two treatments are present. Additionally, this also demonstrates the use of a secondary species, the anti-goat antibody, for enhancing the signal for analyte detection.

EXAMPLE 8

BSA and BSA-Biotin Conjugate Stamped Substrate Tested with Avidin Gold Conjugate BSA and BSA-biotin conjugate were cross-stamped onto a substrate as described above. The resulting cross-stamped slide was immersed in a solution of avidin gold conjugate for 30-60 min and then and washed with PBS (2×2 ml) and ddH$_2$O (2×2 ml) and dried under a stream of N$_2$. The development of diffraction images in both transmission and reflection mode measurements corresponding to BSA-biotin on the substrate was observed visually (data not shown). No diffraction pattern attributable to BSA was observed.

EXAMPLE 9

Figure 8:
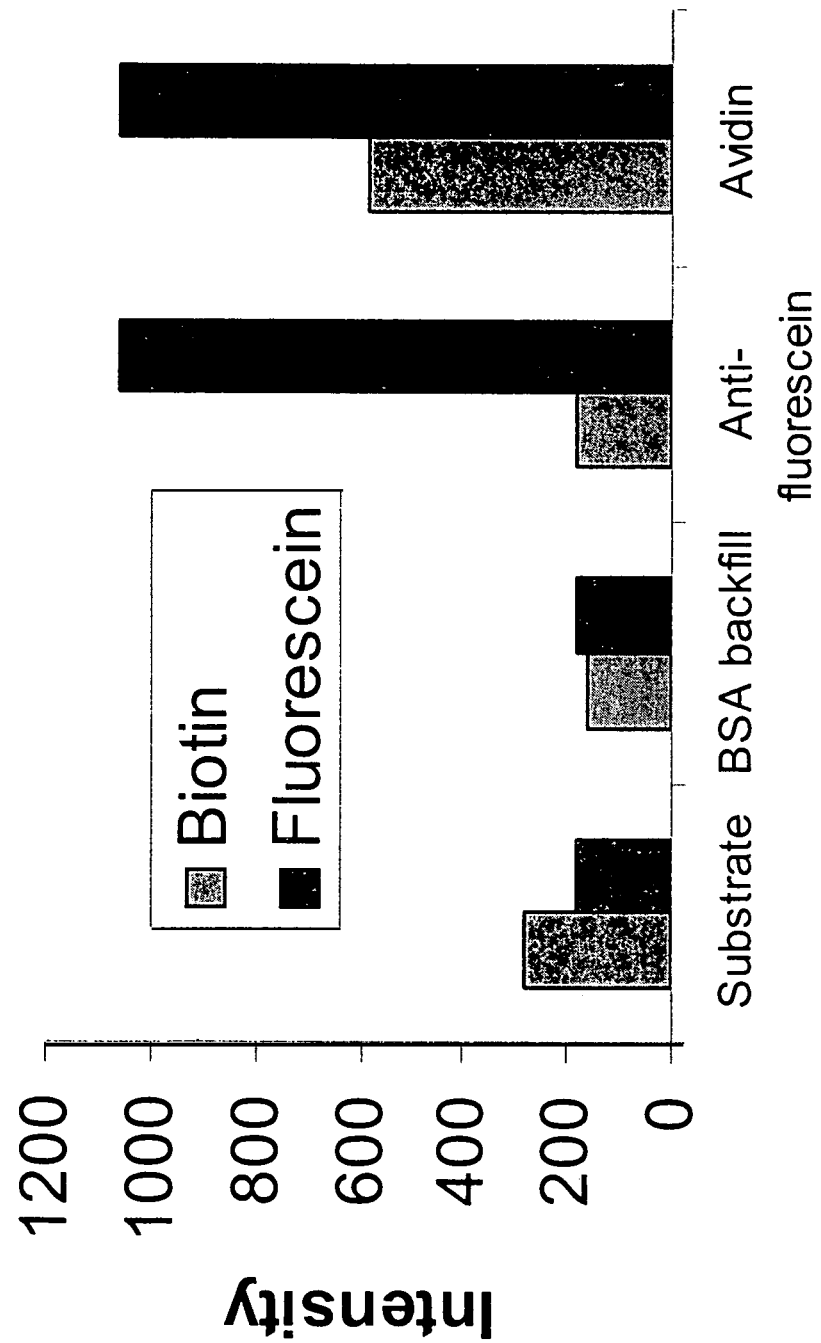
FIG. 8 shows effect of treating a biotin and fluorescein (both as bovin serum albumin (BSA) conjugates) cross-stamped substrate sequentially with the indicated solutions.

BSA-Fluorescein and BSA-Biotin Conjugate Stamped Substrate Tested with Anti-Fluorescein and Avidin BSA-fluorescein and BSA-biotin conjugate were cross-stamped onto a substrate as described above. The resulting cross-stamped slide was immersed in BSA (100 µg/mL in PBS) for 60 min and then washed with PBS (2×2 ml) and ddH$_2$O (2×2 ml) and dried under a stream of N$_2$. The substrate was then immersed in a solution of anti-fluorescein antibody (10% solution of A-889 from Molecular Probes in PBS) for 60 min and then washed with PBS (2×2 ml) and ddH$_2$O (2×2 ml) and dried under a stream of N$_2$. The substrate was then immersed in an avidin solution (~30 µg/mL in PBS) for 60 min and then washed with PBS (2×2 ml) and ddH$_2$O (2×2 ml) and dried under a stream of N$_2$. The intensities of characteristic spots in the diffraction image were measured after each incubation/wash cycle using a linear CCD array detector attached to an oscilloscope. FIG. 8 shows the results. The patterned substrate shows low intensity diffraction signals initially (prior to the introduction of the analyte). Treatment with BSA partially fills in the areas of exposed glass not already covered by stamped BSA-conjugates, reducing the signals further. Addition of a solution of anti-fluorescein antibody results in a dramatic increase in the diffraction signal arising from the stamped fluorescein-BSA conjugate, while little change is observed in the signal that derives from the patterned biotin-BSA conjugate. Finally, addition of a solution of avidin results in the increase in the diffraction signal that arises from stamped biotin-BSA conjugate, while the signal for fluorescein-BSA conjugate is unchanged.

EXAMPLE 10

DNA Hybridization

Figure 9:
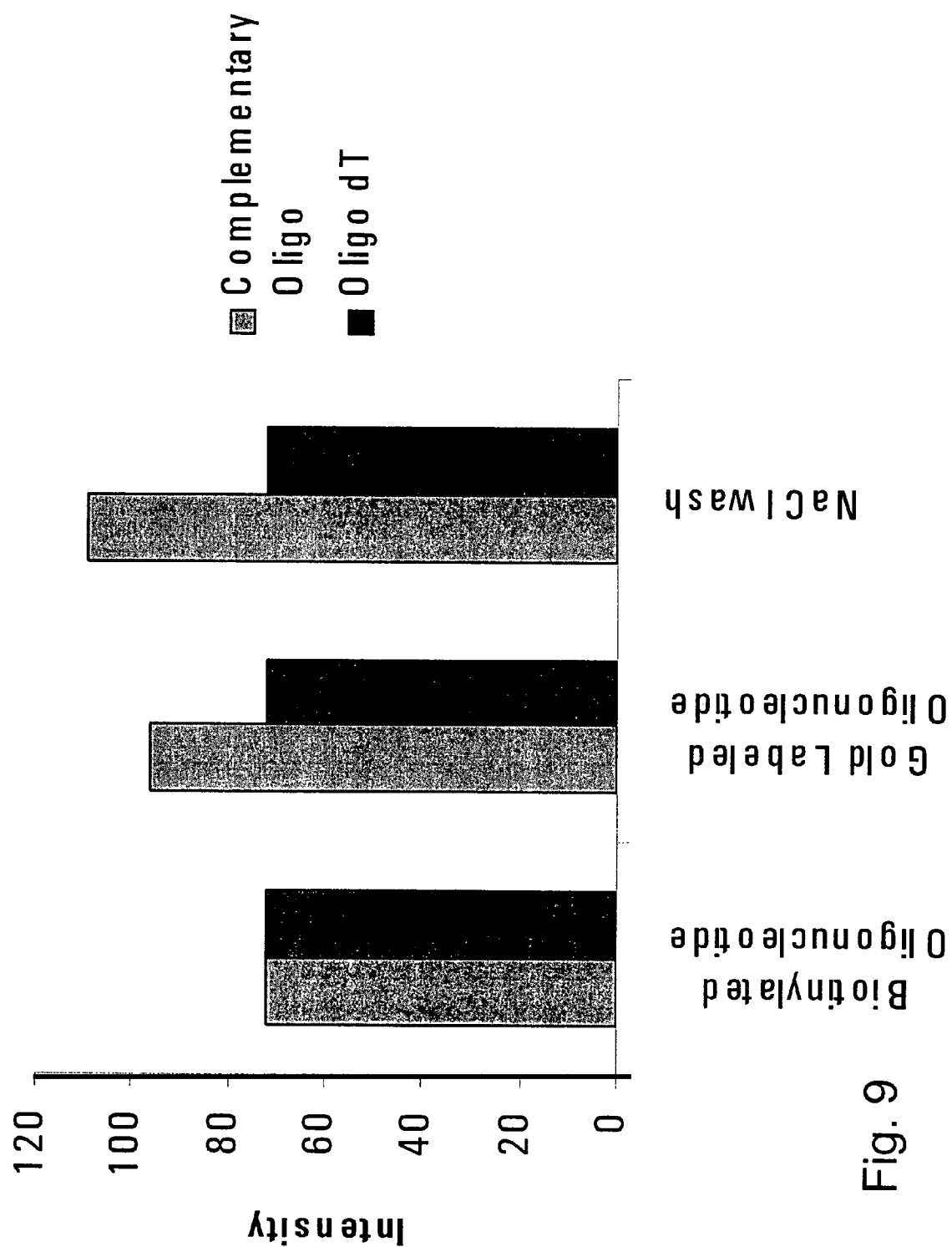
FIG. 9 shows the use of an avidin stamped substrate for the detection of single-stranded DNA by the sequential treatment with the indicated solutions.

A glass slide was stamped with avidin as described above. The resulting patterned slide was immersed in a solution of BSA (50 µg/mL in PBS) for 60 min and then washed with PBS (2×2 ml) and ddH$_2$O (2×2 ml) and dried under a stream of N$_2$. The substrate was then immersed in a 10 µM aqueous solution of biotinylated oligonucleotide 2590BT (5'CAGT-CAGTCAGTCAGTCAGT-biotin-3') for 60 min at room temperature. After washing with PBS (2×2 ml) and ddH$_2$O (2×2 ml) and drying under a stream of N$_2$, the substrate was immersed for 60 min at room temperature in a 10 µM aqueous solution of the colloidal gold-labelled complementary oligonucleotide strand 2593T (5'ACTGACTGACTGACT-GACTG-S-gold-3'). The sample was again washed with PBS (2×2 ml) and ddH$_2$O (2×2 ml) and dried under a stream of N$_2$, before a final 60 min. incubation in 1.0M NaCl. A control experiment using biotinylated oligo-dG(5'-G$_{20}$-biotin-3') instead of 2590BT as the first strand was also performed. FIG. 9 shows the results. The intensity of a characteristic spot in the diffraction image corresponding to the pattered avidin layer was monitored after each incubation/wash cycle with a linear CCD array detector attached to an oscilloscope. The avidin-patterned substrate was initially treated with biotinylated oligonucleotide 2590BT; a small signal at the characteristic spot was observed. Addition of the complementary oligonucleotide 2593T (gold-conjugate) results in an increase in the signal. Further treatment of the substrate with 1.0 M NaCl wash results in a further increase in signal. Finally, as a control, a substrate patterned with avidin was treated initially with a biotinylated poly-dG oligonucleotide instead of 2590BT; the same sequence of treatments did not result in a corresponding increase in signal intensity.

EXAMPLE 11

Titration of Rabbit IgG Stamped Substrate with Anti-Rabbit IgG

Figure 10:
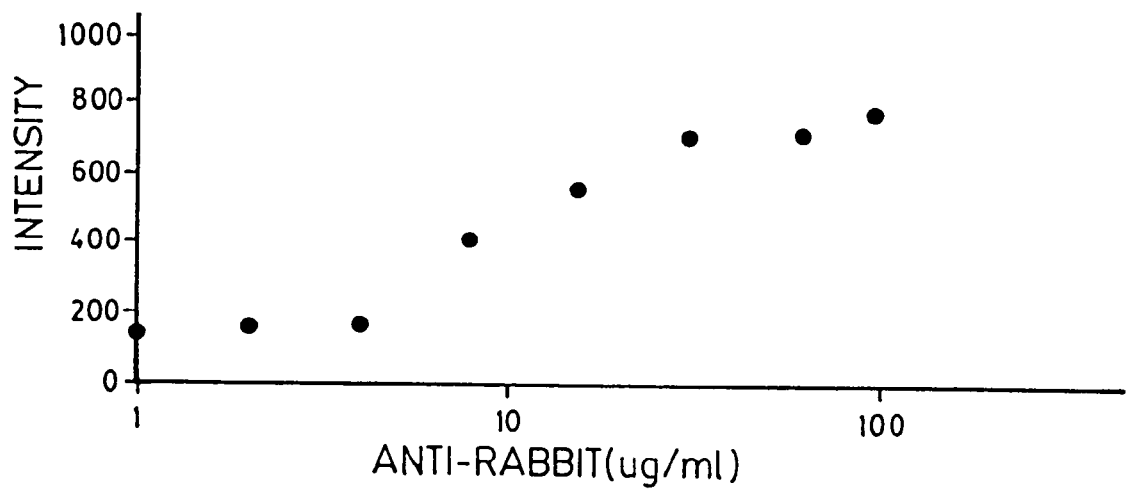
FIG. 10 shows the titration of a substrate patterned with rabbit IgG with increasing concentrations of anti-rabbit IgG.

The substrate was stamped with rabbit IgG as described above. The resulting patterned slide was treated sequentially by incubating with increasing concentrations of anti-rabbit IgG solution for 15 min at room temperature. After each incubation, the substrate was washed with PBS (2×2 ml) and ddH$_2$O (2×2 ml) and dried under a stream of N$_2$. The intensities of two characteristic spots from the resulting diffraction image were measured and averaged after each treatment. FIG. 10 shows the results.

EXAMPLE 12

Time Dependence of Streptavidin Binding to Biotin-BSA Substrate

Figure 11:
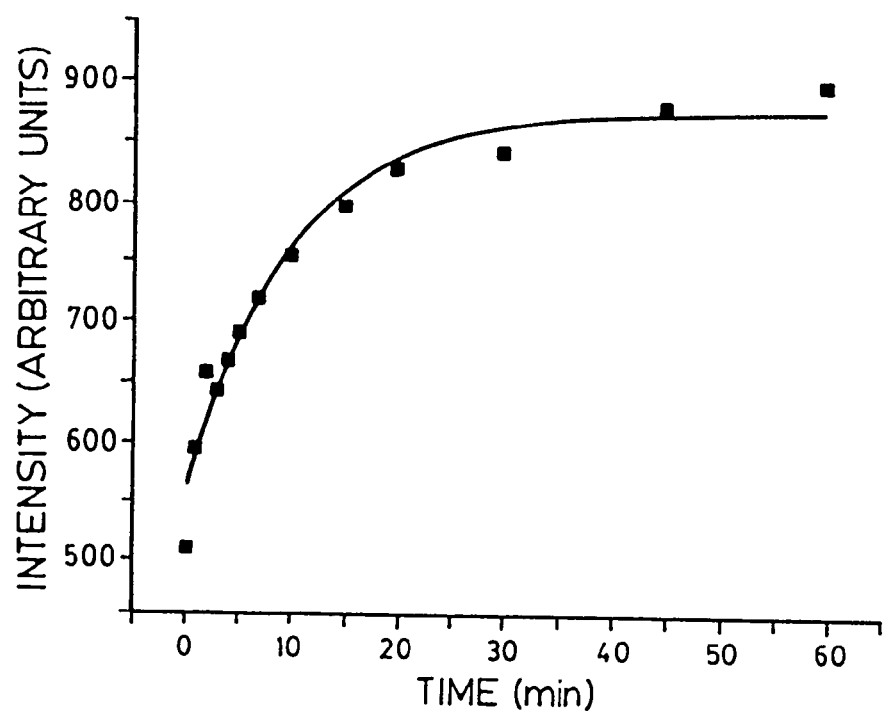
FIG. 11 shows the change in signal over time resulting from the treatment of a biotin-BSA patterned substrate with streptavidin solution.

A glass slide was stamped with biotin-BSA as described above. The resulting patterned slide was placed in a liquid flow cell as shown in FIG. 3c. A solution of streptavidin (500 µL, 200 µg/mL in PBS) was added to the flow cell and the intensity of a characteristic spot from the resulting diffraction image was measured at varying time intervals. FIG. 11 shows the change in signal over time resulting from the treatment of a biotin-BSA patterned substrate with streptavidin solution.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

Therefore what is claimed is:

1. A sensing element for use in a light diffraction assay for detecting the presence or absence of at least two analytes, comprising:
    a substrate including opposed surfaces including analyte-specific receptor patterns formed on both of said opposed surfaces, said patterns formed on each opposed surface including a first pre-selected pattern of first analyte-specific receptors and at least a second pre-selected pattern including second analyte-specific receptors, wherein each of said pre-selected patterns on said surface is distinct from the other pre-selected pattern of analyte-specific receptors formed on the surface and, when bound to an analyte, gives rise to a pre-selected diffraction pattern distinct from diffraction patterns formed from all other unbound and bound pre-selected patterns on the surface.

2. The sensing element according to claim 1 wherein said at least two pre-selected patterns interpenetrate each other in a preselected area on said substrate surface.

3. The sensing element according to claim 1 wherein said at least two pre-selected patterns are located in close proximity to each other but do not interpenetrate each other on said substrate surface.

4. The sensing element according to claim 1 wherein said at least two pre-selected patterns are formed within a selected area on said surface, including a plurality of selected areas on said surface of said substrate with each selected area of said substrate surface having thereon at least two patterns.

5. The sensing element according to claim 1 wherein said analyte-specific receptors are one of a member of a binding pair selected from the group consisting of antibody-antigen, enzyme-inhibitor, complementary strands of nucleic acids or oligonucleotides, receptor-hormone, receptor-effector, enzyme-substrate, enzyme-cofactor, glycoprotein-carbohydrate, binding protein-substrate, antibody-hapten, protein-ligand, protein-nucleic acid, protein-small molecule, protein-ion, cell-antibody to cell, small molecule-antibody to said small molecule, chelators to metal ions and air-born pathogens to associated air-born pathogen receptors.

6. The sensing element according to claim 1 wherein one of the analyte-specific receptors assays for a known standard that is present in a medium to be screened for said analytes.

7. The sensing element according to claim 1 wherein said pre-selected patterns of analyte-specific receptors include surface relief patterns formed directly in the surface of said substrate.

8. The sensing element according to claim 1 including an intervening layer located directly on said surface of said substrate, and wherein said pre-selected patterns of analyte-specific receptor patterns are located on said intervening layer.

9. The sensing element according to claim 8 wherein said intervening layer is a layer of avidin in a pattern, and wherein said analyte-specific receptors are biotinylated analyte-specific receptors to bind with the patterned avidin layer.

10. The sensing element according to claim 1 wherein said substrate is selected from the group consisting of glass, silanized glass, silicon, silicon dioxide, polymer, metal, metal oxide, metal film, metal oxide film, partially or fully reflective substrates including metals, and metal coated substrates.

11. The sensing element according to claim 1 wherein said substrate is a dipstick.

12. The sensing element according to claim 1 wherein said substrate has encoded thereon instructions that identify which analyte-specific receptors are present in said at least two patterns.

13. An apparatus for detection of analytes in a medium using diffraction of light, comprising:
    a source of illumination;
    a sensing element including a substrate having opposed surfaces and on both of said opposed surfaces a first pre-selected pattern of first analyte-specific receptors and at least a second pre-selected pattern including second analyte-specific receptors, wherein each of said pre-selected patterns on said surface is distinct from the other pre-selected patterns of analyte-specific receptors formed on the surface and, when bound to an analyte, gives rise to a pre-selected diffraction pattern distinct from diffraction patterns formed from all other unbound and bound pre-selected patterns on the surface, said source of illumination being positioned so as to illuminate said substrate surface;
    detection means positioned with respect to said sensing element to detect at a position spaced from the substrate surface, an image of diffracted light from the substrate surface; and
    processing means for analysing the image of diffracted light for presence of one or more of the pre-selected diffraction patterns representative of binding of one or more analytes to their associated pre-selected pattern of analyte-specific receptors.

14. The apparatus according to claim 13 wherein said processing means is connected to said detection means and includes storage means for storing signals that are output from said detection means corresponding to said diffracted light, said processing means including image analysis means for deconvoluting said diffraction image.

15. The apparatus according to claim 14 wherein said processing means includes signal processing means for calculating kinetics of interaction of said analytes binding with their analyte-specific receptors from said diffracted light stored as a function of time.

16. The apparatus according to claim 13 wherein the source of illumination produces a coherent and monochromatic collimated beam of light.

17. The apparatus according to claim 13 wherein said source of illumination is a laser with emission at UV, visible, near-infrared or infrared wavelengths.

18. The apparatus according to claim 13 wherein said light illuminating said substrate surface is delivered through an optical fiber.

19. The apparatus according to claim 13 including a cell enclosing a chamber to contain therein said medium being screened for analytes, said cell being adapted to receive said substrate with said selected area of said substrate in contact with said medium, said cell having at least one optical window for light to pass therethrough for detecting for analytes in said medium in situ.

20. The apparatus according to claim 19 wherein the light used to illuminate said surface of said substrate undergoes total internal reflection from the substrate/medium interface.

21. The apparatus according to claim 19 wherein said cell includes a fluid inlet and a fluid outlet for continuous flow of said medium through said cell.

22. The apparatus according to claim 13 wherein the substrate is selected from the group consisting of glass, silanized glass, silicon, silicon dioxide, polymer, metal, metal oxide, metal film, metal oxide film, partially or fully reflective substrates including metals, and metal coated substrates.

23. The apparatus according to claim 13 wherein said detection means is an imaging device.

24. The apparatus according to claim 23 wherein said imaging device is an electronic imaging device.

25. The apparatus according to claim 23 wherein said imaging device is a camera.

26. The apparatus according to claim 13 wherein said detection means includes one of a photodiode detector, a photomultiplier tube, an avalanche photodiode and a position-sensitive photodiode.

27. The apparatus according to claim 24 wherein said imaging device is a matrix array detector.

28. The apparatus according to claim 27 wherein said matrix array detector is a CCD detector array.

29. The apparatus according to claim 13 wherein said analyte specific receptors are one of a member of a binding pair selected from the group consisting of antibody-antigen, enzyme-inhibitor, complementary strands of nucleic acids or oligonucleotides, receptor-hormone, receptor-effector, enzyme-substrate, enzyme-cofactor, glycoprotein-carbohydrate, binding protein-substrate, antibody-hapten, protein-ligand, protein-nucleic acid, protein-small molecule, protein-ion, cell-antibody to cell, and small molecule-antibody to said small molecule, chelators to metal ions and air-born pathogens to associated air-born pathogen receptors.

30. The apparatus according to claim 13 wherein one of the analyte-specific receptors assays for a known analyte that is present in a medium to be screened for said analytes.

31. The apparatus according to claims 13 wherein said analyte-specific receptors are laid out in said patterns directly on the substrate.

32. The apparatus according to claim 13 including an intervening layer formed directly on the surface of said substrate, and wherein said analyte-specific receptor patterns are laid out on said intervening layer.

33. The apparatus according to claim 32 wherein said intervening layer is a layer of avidin in a pattern, and wherein said analyte-specific receptors are biotinylated analyte-specific receptors to bind with the patterned avidin layer.

34. The apparatus according to claim 13 including means for rastering said light source across the surface of said substrate.

* * * * *